United States Patent
Okamoto et al.

(10) Patent No.: US 6,414,203 B1
(45) Date of Patent: Jul. 2, 2002

(54) METHOD OF TREATING 1,1,1,3,3-PENTAFLUOROPROPANE

(75) Inventors: Hidekazu Okamoto; Keiichi Ohnishi, both of Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 09/830,061

(22) PCT Filed: Aug. 23, 2000

(86) PCT No.: PCT/JP00/05654

§ 371 (c)(1),
(2), (4) Date: May 9, 2001

(87) PCT Pub. No.: WO01/14295

PCT Pub. Date: Mar. 1, 2001

(30) Foreign Application Priority Data

Aug. 23, 1999 (JP) ............................................. 11-234980

(51) Int. Cl.[7] ............................................... C07C 17/38
(52) U.S. Cl. ...................................... 570/177; 570/178
(58) Field of Search ................................ 570/177, 178, 570/246, 247

(56) References Cited

U.S. PATENT DOCUMENTS

| 5,856,595 A | * | 1/1999 | Merkel et al. | 570/178 |
| 6,077,982 A | * | 6/2000 | Yates et al. | 570/177 |
| 6,143,938 A | * | 11/2000 | Sievert | 570/177 |

FOREIGN PATENT DOCUMENTS

| JP | 4-300842 | 10/1992 |
| JP | 5-32567 | 2/1993 |

* cited by examiner

*Primary Examiner*—Alan Siegel
(74) *Attorney, Agent, or Firm*—Oblon, Spivak, McClelland, Maier & Neustadt, P.C.

(57) ABSTRACT

A method for reducing the content of unsaturated impurities contained in 1,1,1,3,3-pentafluoropropane (R245fa), while maintaining the loss of R245fa at a minimum level. R245fa containing unsaturated impurities is contacted in a gas phase with chlorine gas in the presence of an activated carbon catalyst, thereby converting the unsaturated impurities to the chlorine addition compounds to reduce the content of the unsaturated impurities.

7 Claims, No Drawings

METHOD OF TREATING 1,1,1,3,3-PENTAFLUOROPROPANE

This application is a 371 of PCT/JP00/05654 filed Aug. 23, 2000.

TECHNICAL FIELD

The present invention relates to a method for treating 1,1,1,3,3-pentafluoropropane (R245fa). Particularly, this invention relates to a method for reducing the content of unsaturated impurities including halogenated hydrocarbons having an unsaturated bond (hereinafter referred to as unsaturated impurities) such as 1-chloro-3,3,3-trifluoropropene (R1233zd) contained in R245fa.

BACKGROUND ART

R245fa is an essential substance having extensive uses including a replacement for 1,1-dichloro-1-fluoroethane (R141b) which is used as e.g. a foaming agent. As disclosed in WO 96/01797, a method for producing such R245fa is known as an industrially effective method, wherein 1,1,1,3,3-pentachloropropane (R240fa) is fluorinated in a liquid phase, preferably, in the presence of an antimony catalyst.

However, it is known that R245fa produced by the above-mentioned method, in many cases, contains a total amount of from 300 to 20,000 ppm (weight) unsaturated impurities such as 1-chloro-3,3,3-trifluoropropene (R1233zd), 1,3,3,3-tetrafluoropropene (R1234ze), 1,2-dichloro-3,3,3-trifluoropropene (R1223x), 1-chloro-1,3,3,3-tetrafluoropropene (R1224zb), 2-chloro-1,3,3,3-tetrafluoropropene (R1224xe) and 2-chloro-3,3,3-trifluoropropene (R1233xf).

The specification of the Panel for Advancement of Fluorocarbon Test (PAFT II) stipulates that the above-mentioned unsaturated impurities, namely halogenated hydrocarbons having an unsaturated bond, should be reduced to not more than 20 ppm in a total amount.

However, among these unsaturated impurities, there are so many compounds having boiling points close to that of R245fa which is an objective compound. Therefore, it is difficult to separate these compounds from R245fa by a usual distillation treatment. Particularly, it is difficult to separate R1233zd from R245fa by means of distillation. If the concentration of R1233zd is reduced by such distillation to the limiting point stipulated by the above-mentioned PAFT II, the distillation yield of R245fa is extremely lowered, which will lead to a large increase in its production cost.

In general, as a method for separating a saturated halogenated hydrocarbon from unsaturated impurities such as unsaturated halogenated hydrocarbons having physical properties similar to those of the saturated hydrocarbon, a method has been recommended wherein a certain extent of separation is carried out by means of distillation, and then, the remaining unsaturated impurities are removed by means of a chemical method. Heretofore, such various chemical methods have been proposed. For example, U.S. Pat. Nos. 2,999,855 and 4,129,603 disclose an oxidation method using aqueous potassium permanganate as an effective method.

In addition, European Patent 370,688 discloses a decomposition method of unsaturated impurities in a gas phase using a metal oxide such as hopcalite. Further, JP-A-5-32567 discloses a method wherein unsaturated compounds are reacted with chlorine gas in the presence of a catalyst such as γ-alumina and activated carbon to convert unsaturated compounds to their chloride compounds.

Further, WO97/37955 discloses a method wherein unsaturated impurities such as the above-mentioned R1233zd contained in R245fa are removed by chlorination with chlorine gas under light irradiation.

However, those conventional methods have the following disadvantages and thus can not be satisfied. Namely, the method using an aqueous solution of potassium permanganate disclosed in U.S. Pat. No. 2,999,855 have problems from an industrial viewpoint as described below: Potassium permanganate is relatively expensive; Disposal treatment of manganese, heavy metal, compound, is required. The objective saturated halogenated hydrocarbon is moved to an aqueous solution phase of potassium permanganate, which will lead to the loss of the saturated halogenated hydrocarbon.

Further, in the method disclosed in the European Patent 370,688, a life time of the metal oxide is relatively short such as 204 hours at longest, and the activity of the metal oxide is also not sufficient, because the unsaturated impurities to be removed remain in substantial quantity even after carrying out the method.

Further, JP-A-5-32567 discloses a method in a broad concept wherein the unsaturated impurities are reacted with chlorine gas in the presence of the catalyst such as γ-alumina and activated carbon to convert them to their chlorinated compounds, which will be then removed. However, R245fa, an objective compound in the method of the present invention, has a relatively low stability against an alkali in comparison with the compounds disclosed in said patent. Therefore, their dehalogenation reactions are likely to occur, and at the same time, their chlorination reactions are also likely to occur in the presence of chlorine gas. Accordingly, it can not be expected by those skilled in the art whether this method is applicable to a case of R245fa.

Further, in the method disclosed in WO97/37955, wherein the impurities are removed by chlorination using chlorine gas under irradiation of light, it is difficult to control such reaction due to a photochlorination reaction. As a result, byproducts caused by the chlorination of R245fa are generated in relatively large amount. For example, the results shown in Table 1 of the Example shows that R235fa, a chlorinated compound of R245fa, will be generated in an amount of not less than 1%, when R1233zd, an unsaturated impurity, is reduced to not more than 100 ppm. Further, when the fluorinated compound which is obtained by the reaction of R240fa with hydrogen fluoride is employed, it is required to remove hydrogen fluoride before the above chlorination reaction, since the light irradiation lamp made of glass is corroded by the remaining hydrogen fluoride.

The object of the present invention is to provide a new effective treating method of R245fa wherein the amounts of R1233zd and/or the above-mentioned other unsaturated impurities are reduced by converting them to other harmless compounds, while the loss of R245fa, an objective compound, is maintained at a minimum level during its treatment.

The another object of the present invention is to provide a new effective treating method of R245fa wherein R1233zd and/or the above-mentioned other unsaturated impurities contained in R245fa are converted to other harmless compounds, which are then removed, whereby the purity of R245fa, an objective compound, can be increased.

DISCLOSURE OF THE INVENTION

The present invention, which has been made to attain the above-mentioned objects, is to provide a method for treating R245fa, which comprises contacting R245fa containing unsaturated impurities including R1233 and/or other halogenated hydrocarbons having a unsaturated bond in a gas phase with chlorine gas in the presence of an activated carbon catalyst, whereby said unsaturated impurities are converted to the chlorine addition compounds to reduce the content of said unsaturated impurities.

In accordance with the present invention, when R245fa is contacted in a gas phase with chlorine gas in the presence of an activated carbon catalyst, preferably, an activated carbon catalyst having an ash content of not more than a particular value, the side reactions can be suppressed at a minimum level in comparison with a case wherein other catalysts such as alumina are employed. The above side reactions are such that R245fa is subjected to a dehydrohalogenation reaction to produce an unsaturated compound, and that R245fa itself is chlorinated to produce chlorinated byproducts such as R235fa. These facts are newly found by the present inventors, and the present invention is based on such facts.

BEST MODE FOR CARRYING OUT THE INVENTION

The details of the present invention will be described with referring to Examples in the following.

R245fa to be treated by the present invention contains unsaturated impurities including chain or cyclic halogenated hydrocarbons having an unsaturated bond such as a double bond and a triple bond between their carbon atoms. Such unsaturated impurities include R1233zd and/or one or at least two kinds of R1234ze, R1223xd, R1224zb, R1224xe, R1233xf, a cis- or trans-type isomer thereof. The amount of the unsaturated impurities contained in R245fa varies depending on their production methods, and is preferably from 200 ppm to 5 wt %, more particularly from 200 ppm to 1 wt %.

R245fa containing such impurities can be produced by various methods. Among them, is preferred the method wherein R245fa is obtained by fluorination of 1,1,1,3,3-pentachloropropane in a liquid phase with hydrogen fluoride in the presence of an antimony catalyst.

When R245fa to be treated in the present invention contains large amounts of unsaturated impurities therein, it is preferred to remove them previously by usual distillation, whereby the total amount of such unsaturated impurities will be preferably reduced to not more than 5 wt %. The amount of each component of the unsaturated impurities is usually from 200 ppm to 1 wt %. It has been found that the total amount of unsaturated impurities after the treatment of the present invention can be reduced to not more than 150 ppm, particularly not more than 100 ppm.

The activated carbon catalyst to be employed in the present invention is not limited so long as it has property of absorbing R245fa and chlorine. However, it is preferred to use the activated carbon catalyst having a large surface area and excellent in acid resistance and halogen resistance. For example, coconut husk activated carbon, lignin activated carbon, coal activated carbon or petroleum activated carbon is preferably employed. Before the activated carbon catalyst is used, it is preferably contacted with e.g. chlorine gas to remove functional groups such as carbonyl groups existing on its surface, since they may impair the activity of the catalyst.

In the present invention, it has been found that an activated carbon having small amounts of ash content is preferred to reduce the generation of the above byproducts, since the ash content in the activated carbon catalyst is concerned with the byproducts generated by e.g. dehydrohalogenation reaction of R245fa which is an objective compound. The ash content is preferably not more than 10 wt %, particularly preferably not more than 5 wt %. Herein, the ash content in an activated carbon is obtained in the following way. Namely, this is calculated by the method described in JIS K1474 (1991)-9.

In the present invention, the procedure in which R245fa containing the unsaturated impurities is contacted with chlorine gas in the presence of an activated carbon catalyst may be either of a fixed bed or a fluidized bed, and the particle size of the activated carbon is suitably determined depending on a reaction apparatus to be used.

The contact ratio of R245fa containing the unsaturated impurities to chlorine gas is preferably such that chlorine gas is from 1 to 100,000 mol, preferably from 1 to 10,000 mol, particularly preferably from 1 to 1,000 mol per mol of the unsaturated impurities contained in R245fa. Too much amount of chlorine gas is not preferred since the substantial amount of R245fa to be treated may be lost. When R245fa is contacted with chlorine gas, an inert gas such as nitrogen gas may be exist at the same time.

The temperature at which chlorine gas is contacted is preferably with in the range from the temperature at which an addition reaction of chlorine to the targeted impurities is carried out, and a chlorination and a decomposition of R245fa to be treated can be suppressed. Thus, such temperature is preferably within the range from the temperature at which R245fa and chlorine gas exist substantially in the gas states to 400° C., and is particularly preferably from 50 to 300° C.

The contact time may vary depending on the kind of the activated carbon catalyst to be employed and the amount of chlorine gas to be contacted with R245fa, and is preferably from 0.01 to 600 seconds, particularly preferably from 0.1 to 180 seconds.

While the contact pressure is not particularly limited, so long as R245fa to be treated and chlorine gas are not liquefied in the reaction procedure, and it is preferably from a little reduced pressure to 10 kg/cm$^2$ (gauge pressure).

In accordance with the treatment by the present invention, the unsaturated impurities such as R1233zd, which has a boiling point close to R245fa and are difficult to separate from R245fa, are converted to chlorine addition compounds, whereby the content of the unsaturated impurities can be reduced enough to be used as it is for some purposes. Further, in some cases, the resulting chlorine addition compounds of the unsaturated impurities have so higher boiling points than those of original unsaturated impurities that it is possible to separate them from R245fa by means of distillation. Thus, the chlorine addition compounds can be removed by distillation, and the resulting R245fa with a high purity can be employed in many uses.

Now, the present invention will be described in further detail with reference to Examples. However, it should be understood that the present invention is by no means restricted by these Examples. Examples 1 and 3–5 are working examples of the present invention, while Example 2 is a comparative example.

EXAMPLE 1

A U-shaped flow type reactor made of Inconel 600 (inner diameter: 2.54 cm, length: 600 cm) charged with 600 ml of the activated carbon catalyst (manufactured by Takeda Pharmaceutical Industry Co., trade name: Shirasagi C2X, ash content: 1.2 wt %) was immersed in an oil bath and was kept at 200° C. Into the reactor, nitrogen gas and chlorine gas were supplied respectively at 100 ml/min and 880 ml/min for 6 hours, whereby unnecessary functional groups existing on the activated carbon was removed. Then, gasified R245fa containing the unsaturated impurities shown in Table 1 was supplied at a rate of 300 ml/min and chlorine gas was supplied at a rate of 3 ml/min into the reactor and are reacted with each other at 150° C.

The resulting reaction gas was passed through a water trap to remove acid components, and the gas components after the reaction were analyzed by FID gas chromatography. The amounts of R245fa, the unsaturated impurities and the chlorinated byproduct (R235fa) of R245fa before and after the reaction were shown in Table 1 with the area % of the gas chromatograph.

N.D in Table 1 means that no component was detected by FID gas chromatography. This is also applied to the following Tables.

TABLE 1

| Substance | Before reaction (%) | After reaction (%) |
|---|---|---|
| R245fa | 99.100 | 99.580 |
| R1234ze | 0.124 | 0.001 |
| R1233zd | 0.544 | N.D |
| R235fa | N.D | 0.076 |

Further, the resulting reaction gas was recovered as 1,000 g of liquid in a trap cooled at −78° C. The recovered liquid was distilled by 2 l distillation apparatus equipped with a packed column having the number theoretical plates of 15. As a result, 980 g of R245fa having a purity of 99.9% was recovered.

EXAMPLE 2

The reaction was carried out in the same manner as in Example 1 except that γ-alumina catalyst was used instead of the activated carbon catalyst and the reaction temperature was 130° C. The resulting reaction gas was passed into a water trap to remove acid components, and the gas components after the reaction were analyzed in the same manner as in Example 1, by FID gas chromatography. The results were shown in Table 2 in the same manner as in Example 1.

TABLE 2

| Substance | Before reaction (%) | After reaction (%) |
|---|---|---|
| R245fa | 99.100 | 97.200 |
| R1234ze | 0.124 | 2.225 |
| R1233zd | 0.544 | 0.001 |
| R235fa | N.D | 0.276 |

EXAMPLE 3

The reaction was carried out in the same manner as in Example 1 except that the reaction temperature was 200° C. The resulting reaction gas was passed in a water trap to remove acid components, and the gas components after the reaction were analyzed in the same manner as in Example 1 by FID gas chromatography. The results were shown in Table 3 in the same manner as in Example 1.

TABLE 3

| Substance | Before reaction (%) | After reaction (%) |
|---|---|---|
| R245fa | 99.100 | 99.720 |
| R1234ze | 0.124 | N.D |
| R1233zd | 0.544 | N.D |
| R235fa | N.D | 0.120 |

The resulting reaction gas was recovered as 1,000 g of liquid in a trap cooled at −78° C. This recovered liquid was distilled with 2 l distillation apparatus equipped with a packed column having the number of theoretical plates of 15. As a result, 970 g of R245fa having a purity of 99.9% was recovered.

EXAMPLE 4

The reaction was carried out in the same manner as in Example 1 except that flow rate of chlorine was 30 ml/min. The resulting reaction gas was passed in a water trap to remove acid components, and the gas components after the reaction were analyzed by FID gas chromatography in the same manner as in Example 1. The results were shown in Table 4 in the same manner as in Example 1.

TABLE 4

| Substance | Before reaction (%) | After reaction (%) |
|---|---|---|
| R245fa | 99.100 | 99.050 |
| R1234ze | 0.124 | N.D |
| R1233zd | 0.544 | N.D |
| R235fa | N.D | 0.598 |

Further, the reaction gas was recovered as 1,000 g of liquid in a trap cooled at −78° C. The recovered liquid was distilled by 2 l distillation apparatus equipped with a packed column having the number of theoretical plates of 15. As a result, 950 g of R245fa having a purity of 99.9% was recovered.

EXAMPLE 5

The reaction similar to that in Example 1 was carried out for a long period of time. The components of the resulting reaction gas after 10 hours and after 3,000 hours were analyzed by FID gas chromatography in the same manner as in Example 1. The amounts of the unsaturated impurities, the chlorinated product and R245fa before the reaction, after 10 hours and after 3,000 hours were shown in Table 5 with the area % of the gas chromatograph.

TABLE 5

| Substance | Before reaction (%) | After 10 hours | After 3,000 hours |
|---|---|---|---|
| R245fa | 99.100 | 99.580 | 99.560 |
| R1234ze | 0.124 | 0.001 | 0.001 |
| R1233zd | 0.544 | N.D | N.D |
| R235fa | N.D | 0.0076 | 0.0078 |

Industrial Applicability

According to the present invention, the amounts of unsaturated impurities contained in R245fa can be effectively reduced, and the loss of R245fa to be treated can be suppressed at a minimum level.

What is claimed is:
1. A method for treating 1,1,1,3,3-pentafluoropropane, which comprises contacting 1,1,1,3,3-pentafluoropropane containing unsaturated impurities including 1-chloro-3,3,3-trifluoropropene and/or other halogenated hydrocarbons having an unsaturated bond in a gas phase with chlorine gas in the presence of an activated carbon catalyst, whereby said unsaturated impurities are converted to the chlorine addition compounds to reduce the content of said unsaturated impurities.

2. The method according to claim 1, wherein the 1,1,1,3,3-pentafluoropropane is obtained by fluorinating 1,1,1,3,3-pentachloropropane with hydrogen fluoride in a liquid phase.

3. The method according to claim 1, wherein the activated carbon catalyst is an activated carbon having an ash content of not more than 10 wt %.

4. The method according to claim 1 or 2, wherein the total amount of the unsaturated impurities contained in 1,1,1,3,3-pentafluoropropane to be treated is from 200 ppm to 5 wt %, and the total amount of the unsaturated impurities contained in treated 1,1,1,3,3-pentafluoropropane is not more than 150 ppm.

5. The method according to claim 1 or 2, wherein the supply ratio of chlorine gas to the unsaturated impurities contained in 1,1,1,3,3-pentafluoropropane is such that chlorine gas is from 1 to 100,000 mol per mol of the unsaturated impurities.

6. The method according to claim 1 or 2, wherein the temperature at which 1,1,1,3,3-pentafluoropropane containing the unsaturated impurities is contacted with chlorine gas is within the range from the temperature at which 1,1,1,3,3-pentafluoropropane and chlorine gas exist substantially in the gas states to 400° C.

7. The method according to claim 1 or 2, wherein the unsaturated impurities are converted to their chlorine addition compounds, and then the resulting chlorine addition compounds are removed by means of distillation.

* * * * *